United States Patent
Liu et al.

(10) Patent No.: US 11,681,839 B2
(45) Date of Patent: Jun. 20, 2023

(54) SYSTEMS AND METHODS FOR MODELING WATER QUALITY

(71) Applicant: The Board of Trustees of The University of Alabama, Tuscaloosa, AL (US)

(72) Inventors: Hongxing Liu, Tuscaloosa, AL (US); Min Xu, Northport, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 389 days.

(21) Appl. No.: 16/943,290

(22) Filed: Jul. 30, 2020

(65) Prior Publication Data
US 2021/0097217 A1   Apr. 1, 2021

Related U.S. Application Data

(60) Provisional application No. 62/908,283, filed on Sep. 30, 2019.

(51) Int. Cl.
   *G06F 30/20*     (2020.01)
   *G06N 20/20*     (2019.01)
   *G06N 5/01*      (2023.01)

(52) U.S. Cl.
   CPC .............. *G06F 30/20* (2020.01); *G06N 5/01* (2023.01); *G06N 20/20* (2019.01)

(58) Field of Classification Search
   CPC .......... G06F 30/20; G06N 20/20; G06N 5/003
   See application file for complete search history.

(56) References Cited

U.S. PATENT DOCUMENTS

2015/0076340 A1*   3/2015   Liang ................. H01J 49/26
                                              250/423 P

OTHER PUBLICATIONS

Liu H, Xu M, Beck R. An ensemble approach to retrieving water quality parameters from multispectral satellite imagery. InIGARSS 2018-2018 IEEE International Geoscience and Remote Sensing Symposium Jul. 22, 2018 (pp. 9284-9287). IEEE. (Year: 2018).*

(Continued)

*Primary Examiner* — Chuen-Meei Gan
(74) *Attorney, Agent, or Firm* — Meunier Carlin & Curfman LLC (57) ABSTRACT

A system, method, device and computer-readable medium for creating an ensemble model of water quality. The ensemble model is generated by determining a set of optimal component models for spectral regions of a body of water, and combining the optimal models. The optimal models can be based on remote sensing data, including satellite imagery. A K-fold partition approach or a global approach can be used to determine the optimal component models, and the optimal component models can be combined through spectral space partition rules to generate an ensemble model of water quality. The ensemble model not only has improved water quality prediction ability, but also has strong spatial and temporal extensibility. The spatial and temporal extensibility of the ensemble model is fundamentally important and desirable for long-term and large-scale remote sensing monitoring and assessment of water quality.

27 Claims, 10 Drawing Sheets

(56) References Cited

OTHER PUBLICATIONS

Berhane TM, Lane CR, Wu Q, Autrey BC, Anenkhonov OA, Chepinoga VV, Liu H. Decision-tree, rule-based, and random forest classification of high-resolution multispectral imagery for wetland mapping and inventory. Remote sensing. Apr. 9, 2018;10(4):580. (Year: 2018).*

Lyons MB, Keith DA, Phinn SR, Mason TJ, Elith J. A comparison of resampling methods for remote sensing classification and accuracy assessment. Remote Sensing of Environment. Apr. 1, 2018;208:145-53. (Year: 2018).*

Johansen R, Beck R, Nowosad J, Nietch C, Xu M, Shu S, Yang B, Liu H, Emery E, Reif M, Harwood J. Evaluating the portability of satellite derived chlorophyll-a algorithms for temperate inland lakes using airborne hyperspectral imagery and dense surface observations. Harmful Algae. Jun. 1, 2018;76:35-46. (Year: 2018).*

Adler-Golden, S., Berk, A., Bernstein, L., Richtsmeier, S., Acharya, P., Matthew, M., Anderson, G., Allred, C., Jeong, L., & Chetwynd, J. (1998). FLAASH, a MODTRAN4 atmospheric correction package for hyperspectral data retrievals and simulations. In, *Proc. 7th Ann. JPL Airborne Earth Science Workshop*, pp. 9-14.

Alawadi, "Detection of surface algal blooms using the newly developed algorithm surface algal bloom index (SABI)," in Remote Sensing of the Ocean, Sea Ice, and Large Water Regions 2010, 2010, vol. 7825, p. 782506: *International Society for Optics and Photonics*.

Augusto-Silva et al., "Analysis of MERIS reflectance algorithms for estimating chlorophyll-a concentration in a Brazilian Reservoir," *Remote Sensing*, vol. 6, No. 12, pp. 11689-11707, 2014.

Bao, Y., Tian, Q., & Chen, M. (2015). A Weighted Algorithm Based on Normalized Mutual Information for Estimating the Chlorophyll-a Concentration in Inland Waters Using Geostationary Ocean Color Imager (GOCI) Data. *Remote Sensing*, 7, 11731-11752.

Beaulieu, J.J., Smolenski, R.L., Nietch, C.T., Townsend-Small, A., Elovitz, M.S., & Schubauer-Berigan, J.P. (2014). Denitrification alternates between a source and sink of nitrous oxide in the hypolimnion of a thermally stratified reservoir. *Limnology and Oceanography*, 59, 495-506.

Beck, R., Xu, M., Zhan, S., Liu, H., Johansen, R.A., Tong, S., Yang, B., Shu, S., Wu, Q., & Wang, S. (2017). Comparison of Satellite Reflectance Algorithms for Estimating Phycocyanin Values and Cyanobacterial Total Biovolume in a Temperate Reservoir Using Coincident Hyperspectral Aircraft Imagery and Dense Coincident Surface Observations. *Remote Sensing*, 9, 538.

Beck, R., Zhan, S., Liu, H., Tong, S., Yang, B., Xu, M., Ye, Z., Huang, Y., Shu, S., & Wu, Q. (2016). Comparison of satellite reflectance algorithms for estimating chlorophyll-a in a temperate reservoir using coincident hyperspectral aircraft imagery and dense coincident surface observations. *Remote Sensing of Environment*, 178, 15-30.

Blondeau-Patissier, D., Gower, J.F., Dekker, A.G., Phinn, S.R., & Brando, V.E. (2014). A review of ocean color remote sensing methods and statistical techniques for the detection, mapping and analysis of phytoplankton blooms in coastal and open oceans. *Progress in oceanography*, 123, 123-144.

Breiman, J. Friedman, R. Olshen, and C. Stone, "Classification and Regression Trees, Wadsworth International Group, Belmont, CA, 1984," *Case Description Feature Subset Correct Missed FA Misclass*, vol. 1, pp. 1-3, 1993.

Bruzzone, Lorenzo, and Farid Melgani. "Robust multiple estimator systems for the analysis of biophysical parameters from remotely sensed data." *IEEE Transactions on Geoscience and Remote Sensing* 43.1 (2005): 159-174.

Dall'Olmo, G., Gitelson, A.A., Rundquist, D.C., Leavitt, B., Barrow, T., & Holz, J.C. (2005). Assessing the potential of SeaWiFS and MODIS for estimating chlorophyll concentration in turbid productive waters using red and near-infrared bands. *Remote Sensing of Environment*, 96, 176-187.

Dietterich, T.G. (2000). Ensemble methods in machine learning. *Multiple classifier systems*, 1857, 1-15.

Doblas-Reyes, F.J., Hagedorn, R., & Palmer, T. (2005). The rationale behind the success of multi-model ensembles in seasonal forecasting-II. Calibration and combination. *Tellus A*, 57, 234-252.

Drusch, M., Del Bello, U., Carlier, S., Colin, O., Fernandez, V., Gascon, F., Hoersch, B., Isola, C., Laberinti, P., & Martimort, P. (2012). Sentinel-2: ESA's optical high-resolution mission for GMES operational services. *Remote Sensing of Environment*, 120, 25-36.

Efron, B., & Tibshirani, R.J. (1994). *An introduction to the bootstrap*. CRC press.

El-Alem, A., Chokmani, K., Laurion, I., & El-Adlouni, S.E. (2014). An Adaptive Model to Monitor Chlorophyll-a in Inland Waters in Southern Quebec Using Downscaled MODIS Imagery. *Remote Sensing*, 6, 6446-6471.

Freund, Y. (1995). Boosting a weak learning algorithm by majority. *Information and computation*, 121, 256-285.

Guanter, L., Ruiz-Verdú, A., Odermatt, D., Giardino, C., Simis, S., Estellés, V., Heege, T., Domínguez-Gómez, J.A., & Moreno, J. (2010). Atmospheric correction of ENVISAT/MERIS data over inland waters: Validation for European lakes. *Remote Sensing of Environment*, 114, 467-480.

Hagedorn, R., Doblas-Reyes, F.J., & Palmer, T. (2005). The rationale behind the success of multi-model ensembles in seasonal forecasting-I. Basic concept. *Tellus A*, 57, 219-233.

Mather, P.M., & Koch, M. (2011). *Computer processing of remotely-sensed images: an introduction*. John Wiley & Sons.

Matthews, M.W. (2011). A current review of empirical procedures of remote sensing in inland and near-coastal transitional waters. *International journal of Remote sensing*, 32, 6855-6899.

Maxwell, Aaron E., Timothy A. Warner, and Fang Fang. "Implementation of machine-learning classification in remote sensing: An applied review." *International Journal of Remote Sensing* 39.9 (2018): 2784-2817.

Memarsadeghi, N., Mount, D.M., Netanyahu, N.S., & Le Moigne, J. (2007). A fast implementation of the ISODATA clustering algorithm. *International Journal of Computational Geometry & Applications*, 17, 654 71-103.

Odermatt, D., Gitelson, A., Brando, V.E., & Schaepman, M. (2012). Review of constituent retrieval in optically deep and complex waters from satellite imagery. *Remote Sensing of Environment*, 118, 116-126.

Olmanson, L.G., Brezonik, P. L., & Bauer, M.E. (2015). Remote sensing for regional lake water quality assessment: capabilities and limitations of current and upcoming satellite systems. *Advances in Watershed Science and Assessment* (pp. 111-140): Springer.

Opitz, D.W., & Shavlik, J.W. (1996). Actively searching for an effective neural network ensemble. *Connection Science*, 8, 337-354.

Pahlevan, N., Chittimalli, S.K., Balasubramanian, S.V., & Vellucci, V. (2019). Sentinel-2/Landsat-8 product consistency and implications for monitoring aquatic systems. *Remote Sensing of Environment*, 220, 19-29.

Perrone, M.P., & Cooper, L.N. (1992). When networks disagree: Ensemble methods for hybrid neural networks. In: *Brown Univ Providence Ri Inst for Brain and Neural Systems*.

Revel, C., Lonjou, V., Marcq, S., Desjardins, C., Fougnie, B., Coppolani-Delle Luche, C., Guilleminot, N., Lacamp, A.-S., Lourme, E., & Miquel, C. (2019). Sentinel-2A and 2B absolute calibration monitoring. *European Journal of Remote Sensing*, 52, 122-137.

Shafique, Naseer A., et al. "Hyperspectral remote sensing of water quality parameters for large rivers in the Ohio River basin." *First interagency conference on research in the watershed*, Benson, AZ. 2003.

Topp, T. M. Pavelsky, D. Jensen, M. Simard, and M. R. Ross, "Research Trends in the Use of Remote Sensing for Inland Water Quality Science: Moving Towards Multidisciplinary Applications," *Water*, vol. 12, No. 1, p. 169, 2020.

Vidot, J., & Santer, R. (2005). Atmospheric correction for inland waters—Application to SeaWiFS. *International Journal of Remote sensing*, 26, 3663-3682.

Wang, S., & Yao, X. (2009). Diversity analysis on imbalanced data sets by using ensemble models. In, *2009 IEEE Symposium on Computational Intelligence and Data Mining* (pp. 324-331): IEEE.

(56) References Cited

OTHER PUBLICATIONS

Watanabe, F., Alcantara, E., Rodrigues, T., Rotta, L., Bernardo, N., & Imai, N. (2017). Remote sensing of the chlorophyll-a based on OLI/Landsat-8 and MSI/Sentinel-2A (Barra Bonita reservoir, Brazil). *Anais da Academia Brasileira de Ciências*, 0-0.

Xu, M., Liu, H., Beck, R., Lekki, J., Yang, B., Shu, S., Kang, E.L., Anderson, R., Johansen, R., & Emery, E. (2018). A spectral space partition guided ensemble method for retrieving chlorophyll-a concentration in inland waters from Sentinel-2A satellite imagery. *Journal of Great Lakes Research*, vol. 45, No. 3, pp. 454-465, 2019.

Zhou, L., Lai, K.K., & Yu, L. (2010). Least squares support vector machines ensemble models for credit scoring. *Expert Systems with Applications*, 37, 127-133.

Zhou, Z.-H., Wu, J., & Tang, W. (2002). Ensembling neural networks: many could be better than all. 748 *Artificial intelligence*, 137, 239-263.

\* cited by examiner

SYSTEMS AND METHODS FOR MODELING WATER QUALITY

CROSS-REFERENCE TO RELATED APPLICATION

This application claims priority to and benefit of U.S. provisional patent application Ser. No. 62/908,283 filed Sep. 30, 2019, which is fully incorporated by reference and made a part hereof.

GOVERNMENT SUPPORT CLAUSE

This invention was made with Government support under Grant NNC16MF95P awarded by the National Aeronautics and Space Administration. The Government has certain rights in the invention.

BACKGROUND

Remote sensing technology is used in a variety of applications, including measuring atmospheric, soil, and water conditions. Typical remote sensors include satellite and aerial imaging systems. The accuracy of a remote sensing technology depends on the model that is used to convert sensor data into predictions of a desired quantity. Typical models use a single modelling system to evaluate data from an entire measured region. Using a single model may be inaccurate, especially when used to evaluate a large region where many different sub-regions contain unique characteristics. This is particularly true for building models of bodies of water based on remote sensing technology.

Empirical models have been widely used to estimate chlorophyll-a (Chl-a) concentration as the proxy variable for algal blooms from multispectral and hyperspectral remote sensing data, due to their simplicity in calibration and implementation and the efficiency in computation. Commonly, a regression technique is utilized to establish an empirical model that relates a spectral index created from remote sensing data (e.g., single bands or band ratios) to a water quality parameter (e.g., Chl-a, turbidity, or colored dissolved organic matter) measured in situ during the remote sensor overpass. In the past, empirical models based on green and blue spectral bands of satellite data have been successfully applied to open ocean waters (Case I waters) for Chl-a retrieval. To better estimate Chl-a concentration in optically complex coastal and inland waters (Case II waters), a wide range of empirical models utilizing the red and near-infrared (NIR) bands have been developed.

The common practice of most previous techniques is to calibrate and evaluate various empirical models and select one single empirical model that has the best overall accuracy and apply it to the entire water body under study. In reality, optical properties of inland waters are complex and highly vary across space and time. Although the selected single empirical model may have the best overall estimation accuracy, it may perform poorly for some portions of the water body. The best single model is often a compromised selection result, and its performance is limited for retrieving water quality parameters. It should be pointed out that an empirical model calibrated for a specific water body in a certain season usually cannot be applied to the same water body in a different season, nor to other water bodies even for the same season. In other words, traditional empirical models are not spatially or temporally extensible. The lack of extensibility over space and time imposes strict and expensive demand for in situ water-truth data acquisition during the overpasses of spaceborne or airborne sensors, hence hindering the application of the remote sensing technology for long-term water quality monitoring at a regional or national scale.

Therefore, what is needed is a system for applying multiple models to a single body of water. In particular, systems and methods for combining multiple models to generate an ensemble model with high prediction accuracy and strong spatial and temporal extensibility.

SUMMARY

To improve the prediction accuracy and to overcome the limitation in spatial and temporal extensibility of individual empirical models, systems, methods and devices are disclosed which use an ensemble method to synergistically combine the advantages of various empirical models using spectral space partition rules. The ensemble model using multiple models based on different physical mechanisms are dynamically adaptable to a wide range of water conditions over space and time, thus producing predictions that are more accurate, consistent, and reliable than any of the individual models used alone.

Methods, systems and devices are described herein that use multispectral images and in situ water quality data to generate an ensemble model of water quality for a body of water to enhance the accuracy and extensibility of water quality predictions.

An example method for generating an ensemble model of water quality is shown and described herein. A number of measuring devices are used to collect water quality data of a body of water. Combined with the water quality data, the multispectral images are then processed by modelling systems to predict attributes of the body of water throughout the body of water. A machine learning modeling system is applied to the set of individual models to optimally model the body of water by mapping each model onto a subsection of the body of water.

For example, due to the complex optical properties of inland waters, it is difficult to accurately retrieve Chl-a concentration in different regions of a water body with one single empirical model. The calibrated single empirical model for this water body often cannot be applied to other water bodies nor to the same water body but in a different time. To overcome the limitations of traditional empirical models in prediction ability and spatio-temporal extensibility, this system and method applies an ensemble method that synergistically combines a set of heterogeneous empirical models based on the spectral space partition rules. The ensemble model not only significantly improves the prediction accuracy compared with traditional empirical models, but also possesses the desirable spatial and temporal extensibility, which traditional empirical models lack. The calibrated ensemble model can be re-used for different regions and different time periods without the expensive demand for additional in situ water quality data. The strong spatial extensibility of the ensemble model would boost the water quality remote sensing applications at regional, national and even global scales and its strong temporal extensibility would facilitate consistent long-term remote sensing monitoring of water quality.

The ensemble model can be implemented in different strategies in terms of how the component models should be calibrated and what kind of component models should be included in the ensemble model base. An iterative K-fold approach is used for constructing the optimal component empirical models in the ensemble. The iterative K-fold calibration approach not only yields an ensemble model with higher prediction accuracy but also leads to the more compact and simpler spectral partition rules, in comparison with the global calibration approach. Furthermore, the increasing heterogeneity of the ensemble model base improves the performance of the resulting ensemble model.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized, including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture, including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Figure 1:
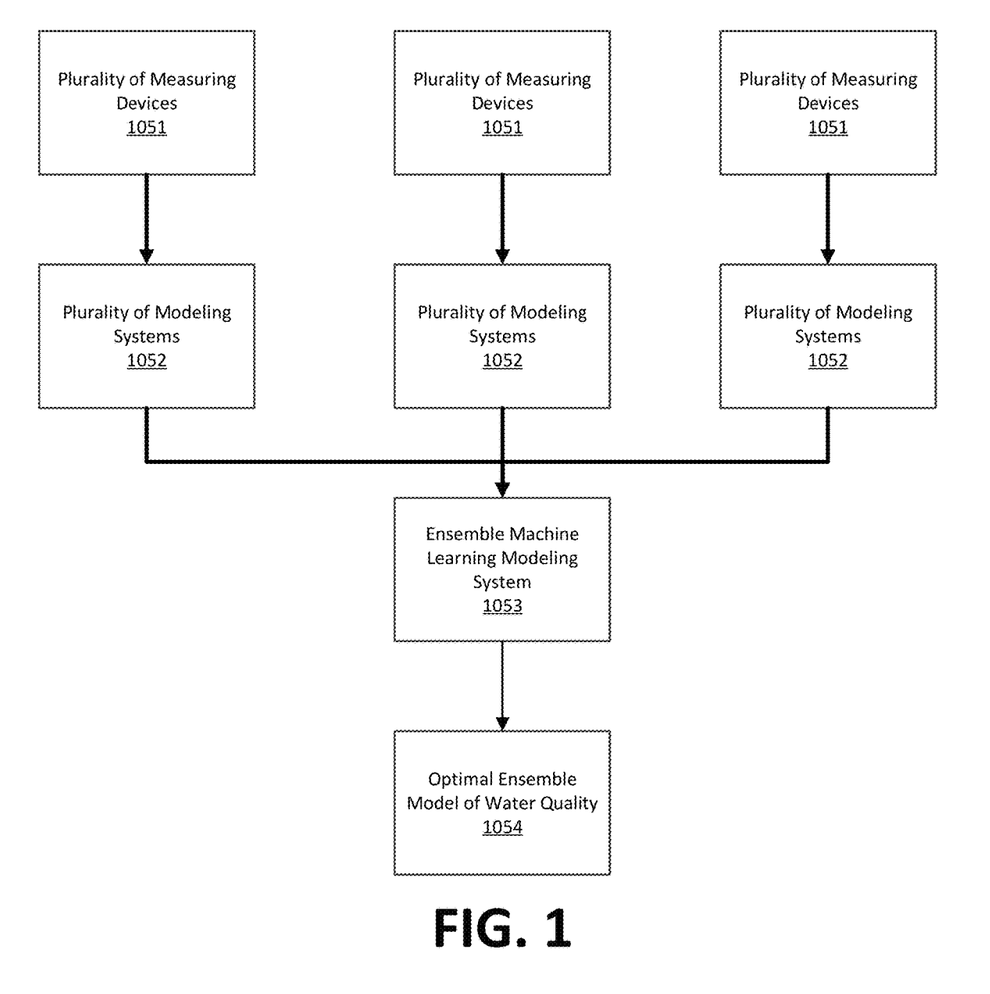
FIG. 1 is a block diagram illustrating the relationship between the measuring devices, models, machine learning system and the final model of water quality.

FIG. 1 is a block diagram of a non-limiting illustration of one configuration of the system for generating an optimal ensemble model of water quality 1054 for a body of water. As shown in FIG. 1, a plurality of measuring devices 1051 are used to acquire water quality data. In some instances, the measuring devices may be remote sensing devices such as satellite imaging systems. Alternatively, measuring devices may be mounted on different platforms, including manned and unmanned aerial vehicles. In some instances, the measuring devices may generate multispectral images periodically or continuously. The water quality data acquired may be in the form of point measurements collected by a multi-parameter water quality sonde (for example, a YSI 6600 multi-parameter sonde (Yellow Springs Instrument, Inc.)). In some instances, the multispectral instrument may operate across a wide spectrum with spectral bands covering from visible to near infrared, and have a resolution of 10 meters. Some or all of the data may be processed and filtered to reduce noise or otherwise improve the quality of the data. Modeling systems 1052 are calibrated based on empirical data from the body of water. In some instances, the modeling system 1052 may include a two-band algorithm (2BDA), a three-band algorithm (3BDA), normalized difference chlorophyll index algorithm (NDCI), slope algorithm (SL), surface algal bloom index algorithm (SABI), fluorescence line height violet algorithm (FLH Violet), blue-green algorithm (BG), and red-green algorithm (RG) models. In some instances, the modeling systems 1052 are calibrated using a global approach, while in other instances the modeling systems 1052 are calibrated using an iterative K-fold partition approach.

Figure 2:
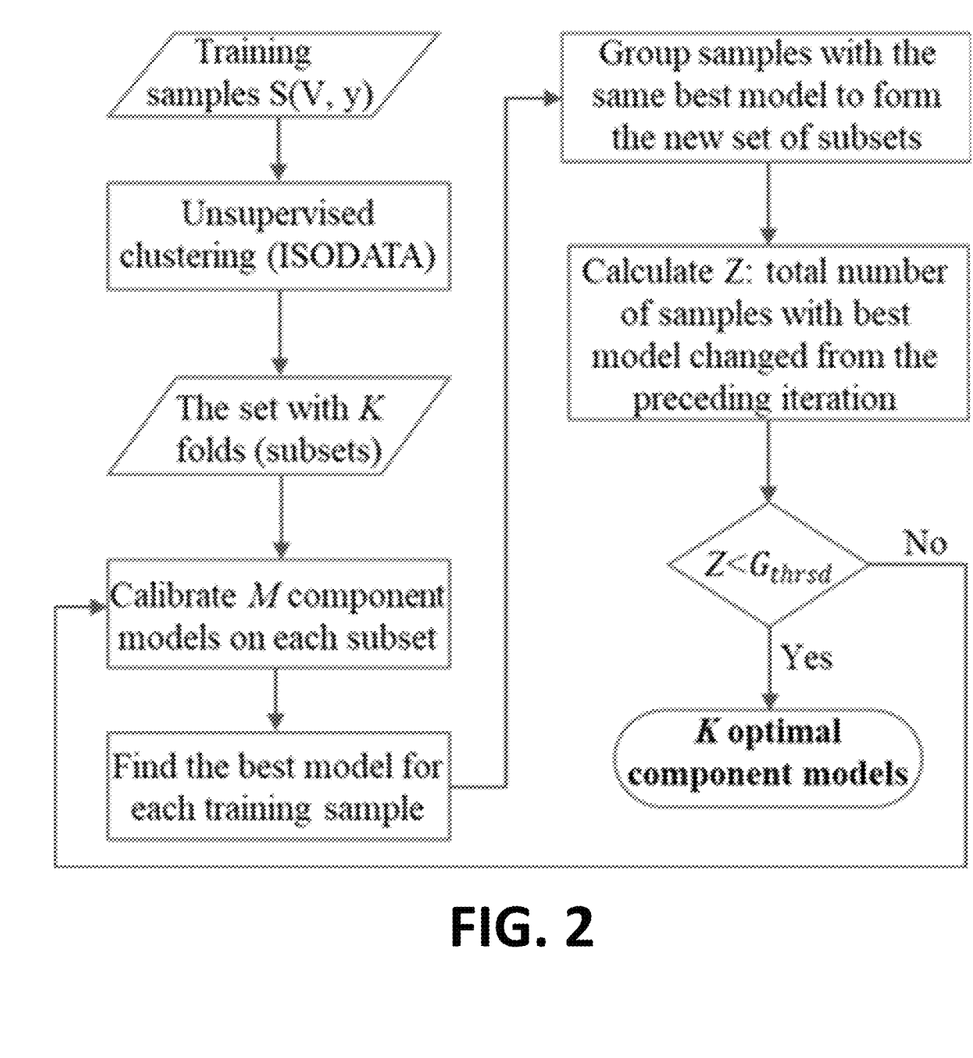
FIG. 2 is an illustration of an iterative K-fold approach to calibrating component empirical models to be included in the ensemble.
Figure 3:
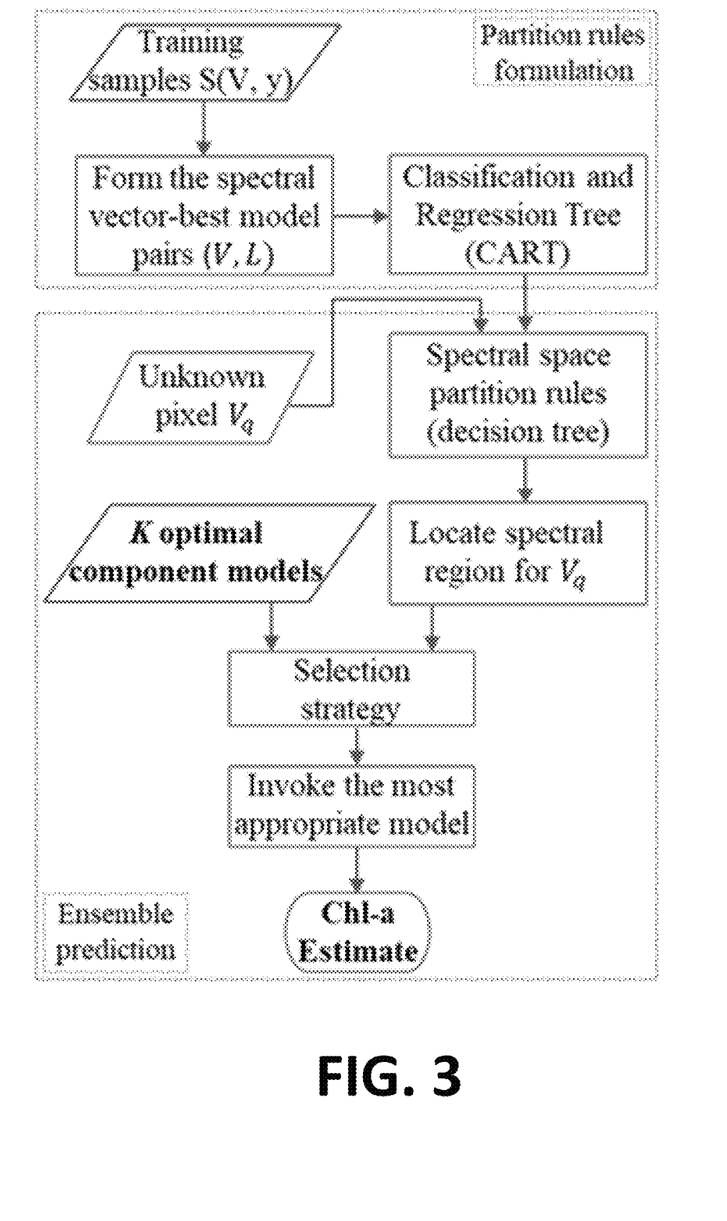
FIG. 3 is an illustration of the formulation of a spectral space partition guided ensemble model for making new predictions.

Spectral space partition rules are used to identify one or more spectral regions of the body of water based on one or more optical characteristics of the body of water. The plurality of optimal component empirical models may be generated by measuring a plurality of water quality measurements, generating a plurality of models, and constructing the plurality of optimal component empirical models from the plurality of models. The optimal component models may be generated by applying an iterative K-fold calibration approach (as shown in FIG. 2). Further, the machine learning modeling system 1053 may apply the ensemble function or spectral space partition-based selection rules to determine the most accurate model (as shown in FIG. 3) 1054.

In a non-limiting example, the spectral space partition-based selection rules are built using Classification and Regression Tree (CART) method and applied to an unknown site for predicting Chl-a. It is assumed that the spectral space defined by a number of spectral bands can be partitioned into a set of spectral regions, and each spectral region corresponds to a component model that gives the best Chl-a estimation result. After the calibrations of component empirical models, for each training sample site ($1 \leq i \leq N$), the best performed component empirical model $L_i$ can be identified to form the pair $(V_i, L_i)$, where $V_i$ is the spectral vector. The spectral space partition rules were established based on $(V_i, L_i)$ pairs to ensure that a specific component empirical model performs the best for each spectral region. In other words, each spectral region serves as the territory of a specific empirical model, and inside this spectral region that specific empirical model produces a more accurate estimate than any other component empirical models. The spectral space partition rules are constructed through establishing a classification tree with a splitting process. At each split, the impurity measure is minimized, and subsets of the split are recursively obtained until the minimum number of samples in the subset or the maximum depth of the tree is reached. Once the spectral partition rules are constructed, for an unknown site (pixel) q with a spectral band vector $v_q$, the spectral space partition rules were employed to find which spectral region the candidate site (pixel) is located. Then, the optimal component empirical model associated with that spectral region is selected and invoked to produce the most accurate Chl-a estimate for the unknown site.

Figure 4:
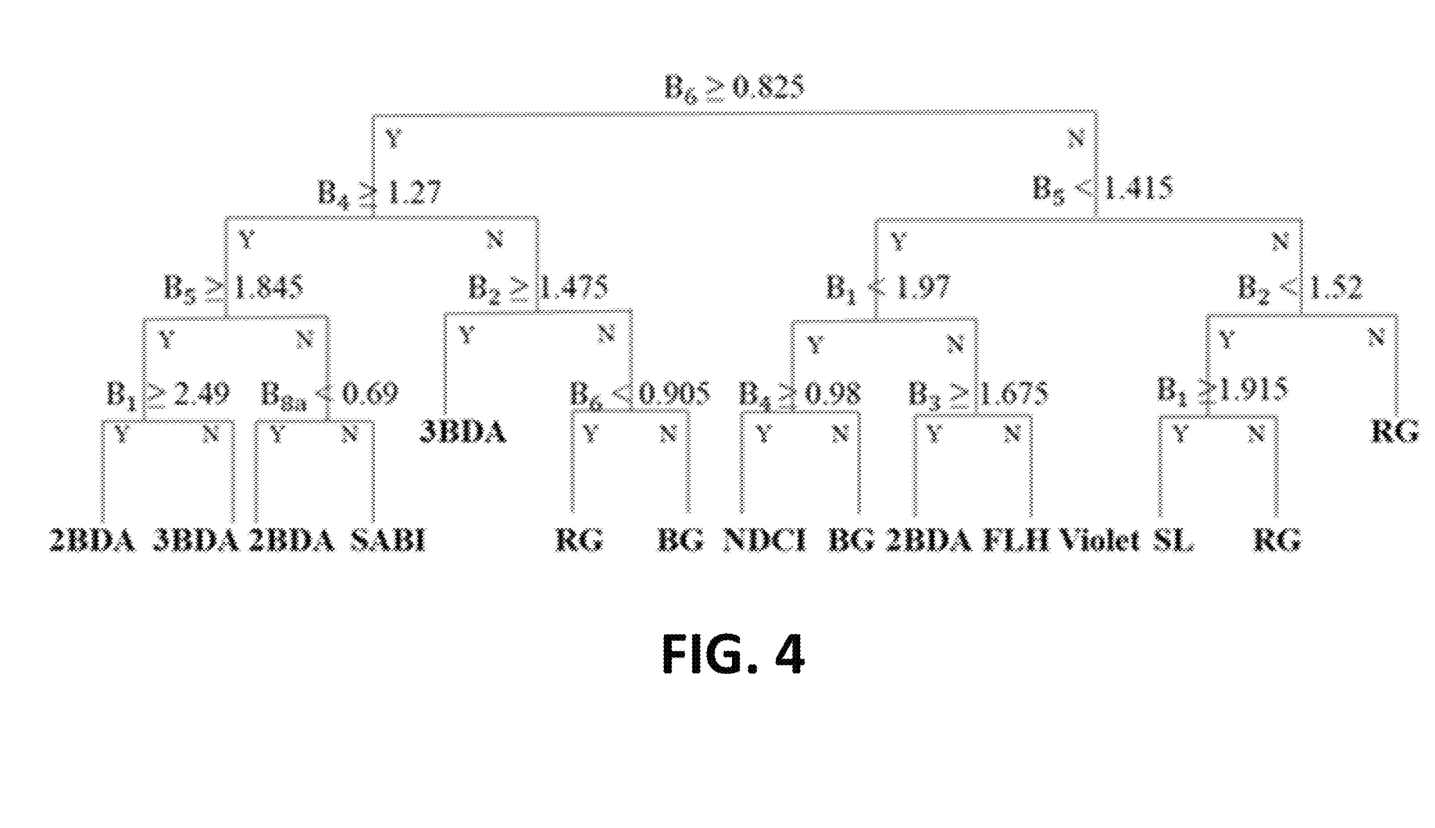
FIG. 4 is an illustration of spectral space partition rules for globally calibrated component models.

Example of spectral space partition rules for globally calibrated component models are shown in FIG. 4. The globally calibrated component models are based on all the training samples. In a non-limiting example, the set of empirical models $e_j(S)$ (j=1, 2, ..., M) is trained independently on the available training set S. The training set S includes N samples: $S=\{(V_1, y_1), (V_2, y_2), ..., (V_i, y_i) ..., (V_N, y_N)\}$. $V_i=\{B_i^1, B_i^2, ..., B_i^P\}$ represents the spectral band vector with a dimension of P for sample site i, and $y_i$ is the measured Chl-a concentration at sample site i. In some instances, the optimal parameters of each global component model are determined by minimizing the sum of squared residuals between the model estimates and the corresponding actual Chl-a measurements for all training samples.

Figure 5:
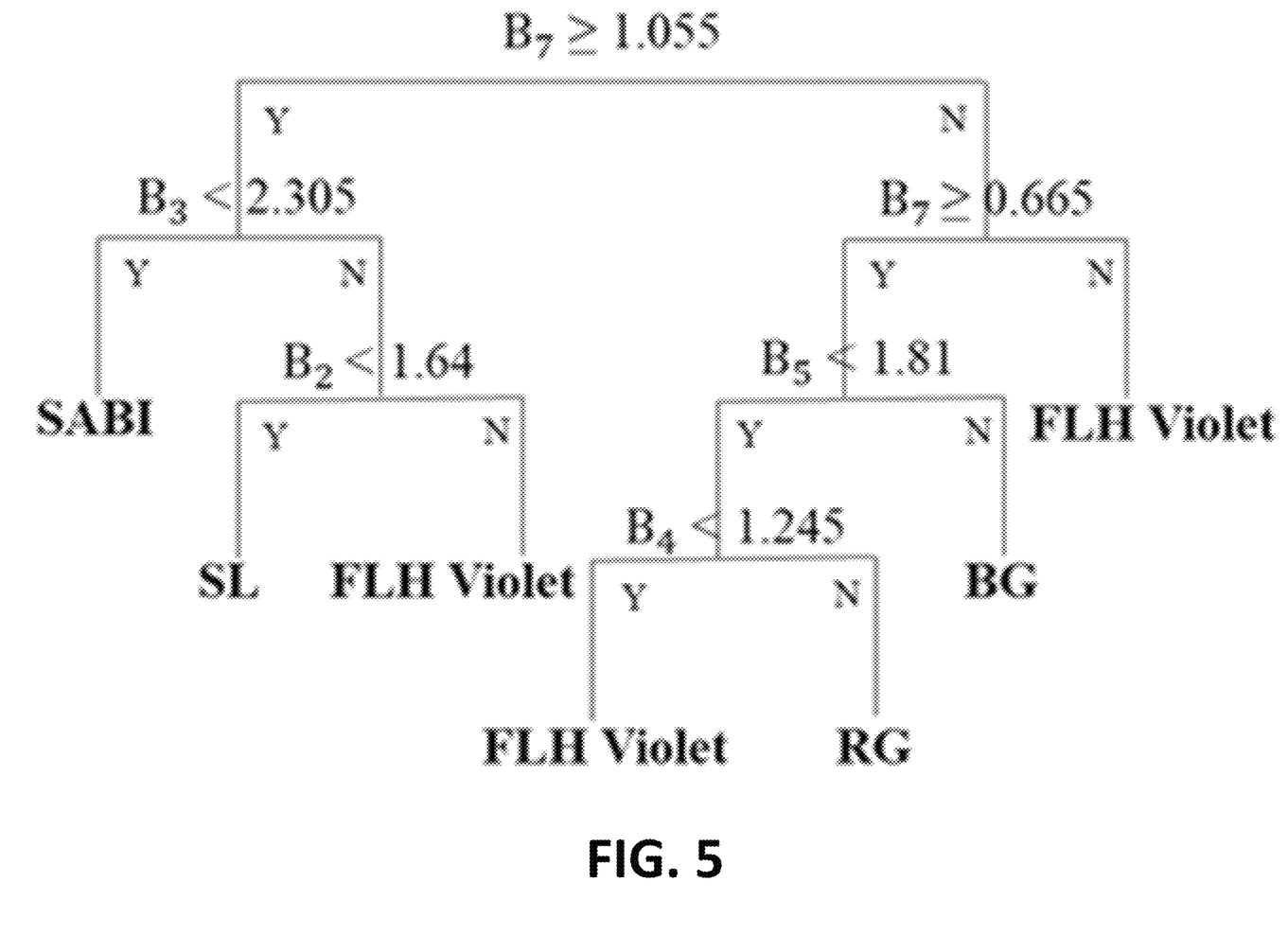
FIG. 5 is an illustration of spectral space partition rules for iterative K-fold calibrated component models.

Examples of spectral space partition rules for iterative K-fold calibrated component models are shown in FIG. 5. The iterative K-fold calibrated component models are generated by a K-fold partition and calibration of the training sample (see FIG. 2). The training set is partitioned into K folds which are subsets of the training data. The K folds in some instances are partitioned in terms of the spectral vector of training samples using an unsupervised clustering technique. Further, in some instances, this unsupervised clustering technique is the iterative self-organizing data analysis technique.

In a non-limiting example, the iterative self-organizing data analysis technique is used to partition the remote sensing data into three subsets with 20 iterations. In this example, eight individual models were calibrated separately on each subset of the training sample, and the best calibrated model in the iteration is determined. All the training samples were partitioned again into a number of subsets in terms of their best empirical model, and those training samples with the same best empirical model were allocated to the same subset. Then, the eight candidate empirical models were calibrated separately on each of the newly formed subsets. This iterative partition and calibration process continued until the convergence criteria was satisfied.

At each iteration, the total number (Z) of samples whose best empirical model change from the preceding iteration is counted and tracked. When Z is less than a threshold ($G_{thrsd}$), this iterative calibration process is considered to be converged and the iterative process will be terminated. In a non-limiting example, $G_{thrsd}$ is set to be 5% of the total number of training samples N. In this example, the number of training samples that have their best model change between the preceding iteration and current iteration is reducing, being 0 between $6^{th}$ and $7^{th}$ iteration, which satisfies the convergence criterion (<5% of the total training samples). After the convergence, five component models survived, each as the best model for a subset of training samples at the final iteration.

Figure 6:
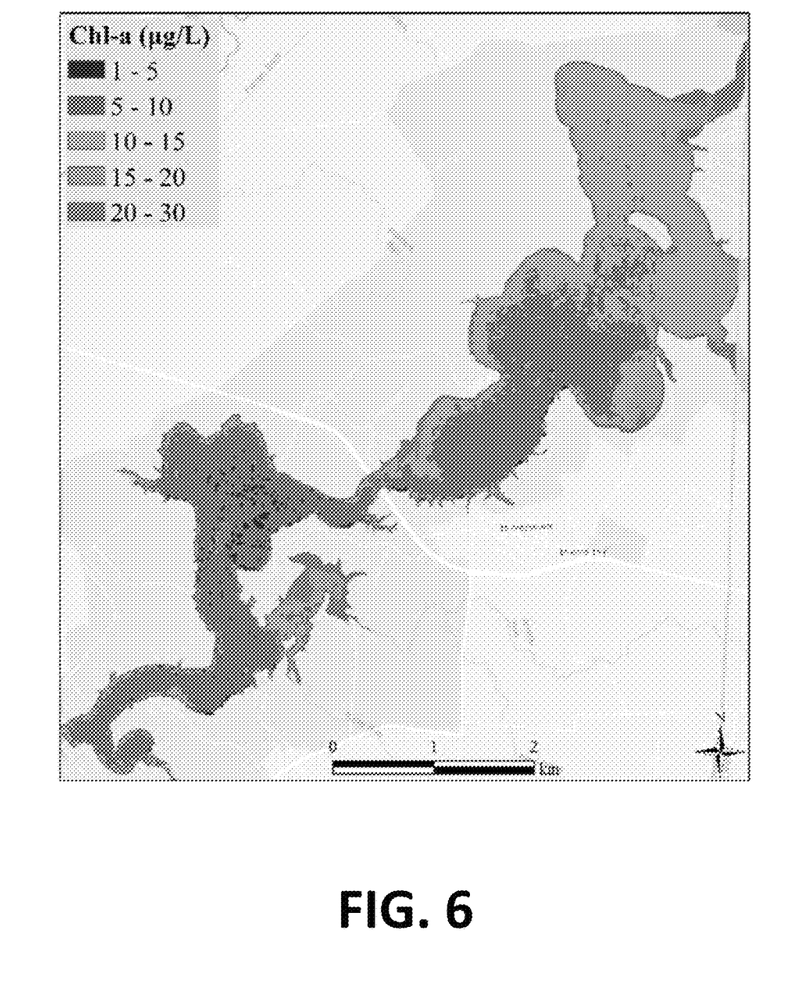
FIG. 6 is an illustration of an experimental result on spatial extensibility, showing the distribution of Chl-a in a body of water predicted by the K-fold ensemble model calibrated for another water body on the same day.
Figure 7:
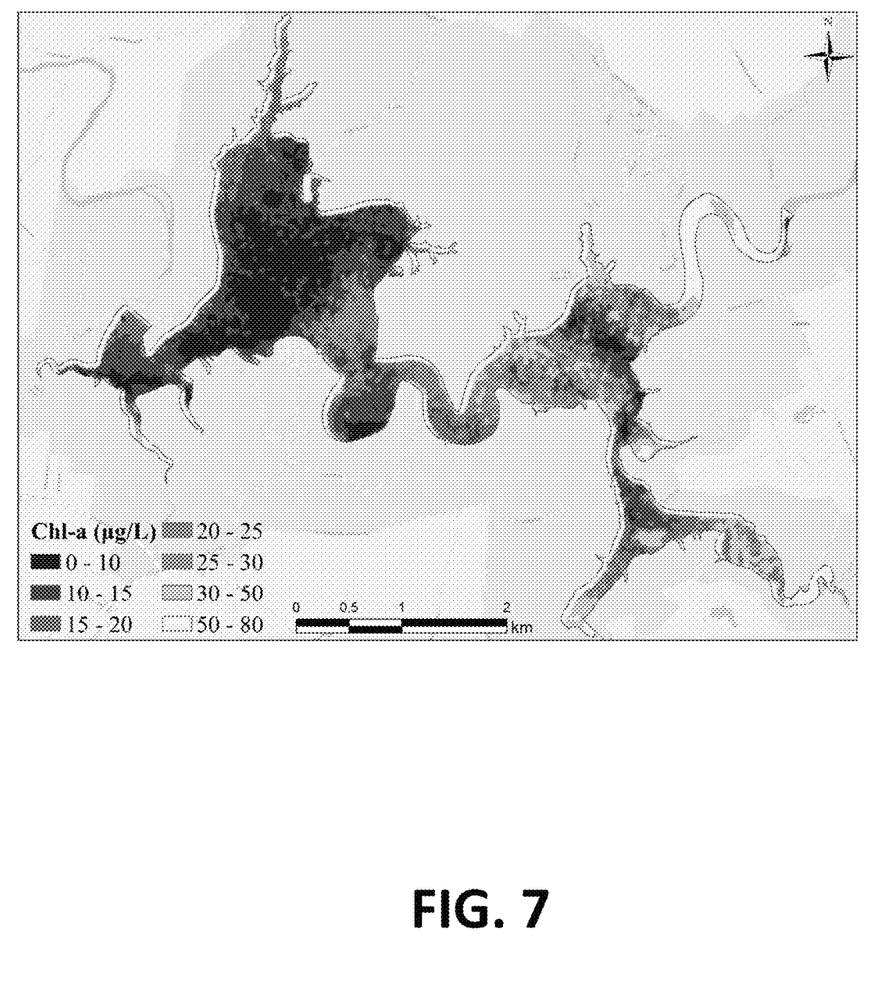
FIG. 7 is an illustration of an experimental result on temporal extensibility, showing the distribution of Chl-a in a body of water predicted by the K-fold ensemble model calibrated on another date for the same water body.

FIG. 6 shows the resulting estimate of water quality produced by applying the K-fold ensemble model calibrated for a specific water body to a different body of water on the same day. FIG. 7 is an illustration of an experimental result on temporal extensibility, showing the distribution of Chl-a in a body of water predicted by the K-fold ensemble model calibrated on another date for the same water body.

Figure 8:
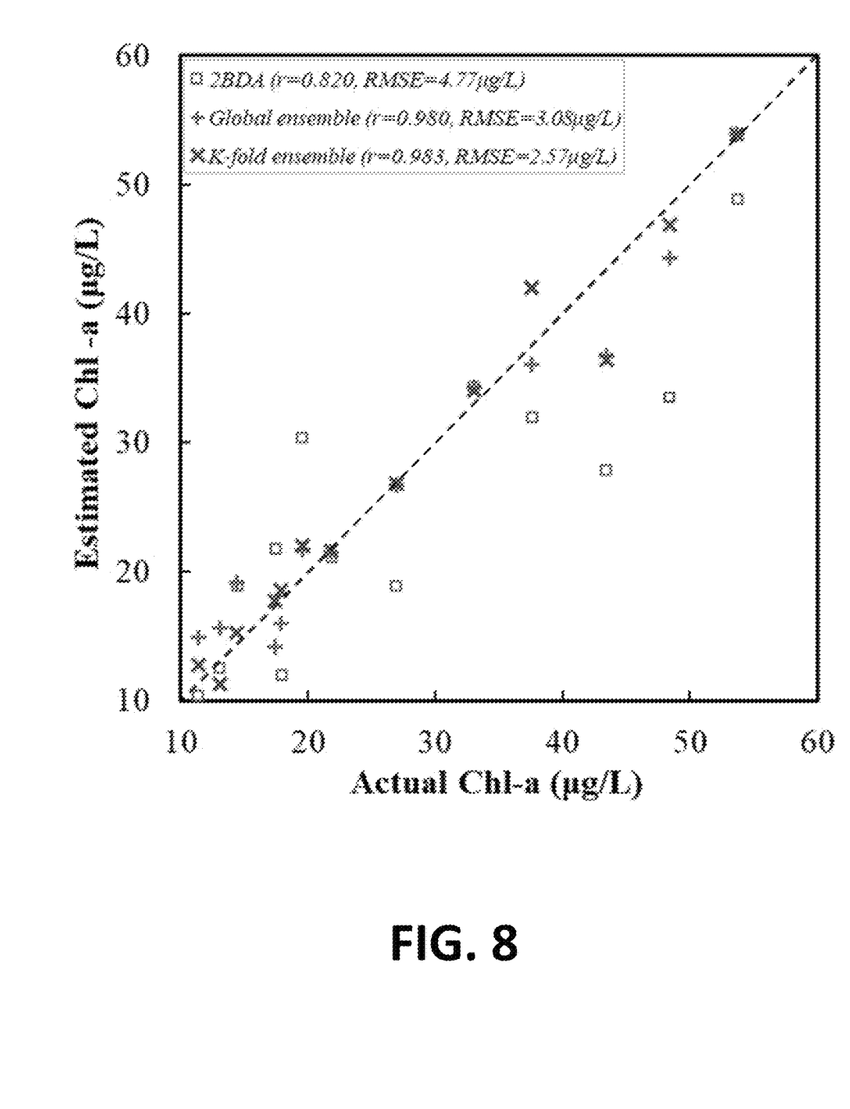
FIG. 8 is an illustration of experimental data comparing the estimated and actual Chl-a values for an individual model, global ensemble model, and K-fold ensemble model.

The Chl-a estimates derived from the best traditional empirical model (2BDA), global ensemble model, and K-fold ensemble model and the actual Chl-a measurement are compared in FIG. 8. In a non-limiting example, actual Chl-a concentrations were obtained from sites within a test body of water. FIG. 8 shows that the K fold ensemble model generates superior estimates of water quality. In FIG. 8, actual and predicted Chl-a concentrations are plotted. In a perfect model, actual Chl-a concentrations would match estimated Chl-a concentrations, and the results would fall on the dashed diagonal line. FIG. 8 shows that the K fold ensemble model produces results superior to the global ensemble model in one instance. Also, both ensemble models outperformed the traditional empirical model.

Figure 9:
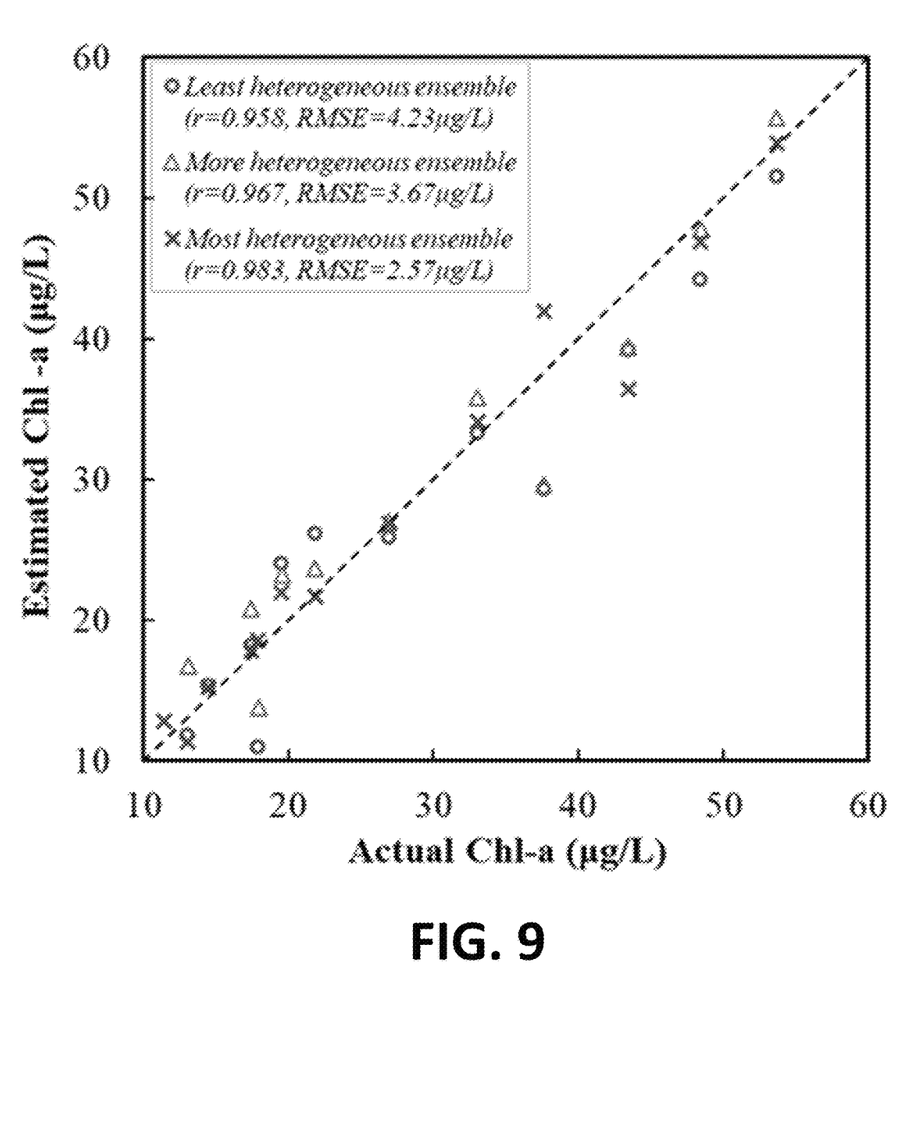
FIG. 9 is an illustration of experimental data comparing the estimated and actual Chl-a values for the least heterogeneous ensemble model, more heterogeneous ensemble model, and the most heterogeneous ensemble model (the original K-fold ensemble model).

The heterogeneity of candidate component models in the ensemble model base also may alter the characteristics of the resulting ensemble model. In the non-limiting example of an ensemble model for Chl-a prediction, higher levels of component model heterogeneity may produce better ensemble model performance. FIG. 9 shows a comparison of three different ensemble models where each model has a different level of heterogeneity. The original K-fold ensemble model is the most heterogenous ensemble model, and in this instance was the most accurate predictor of water quality.

The spectral regions are associated with the plurality of optimal component empirical models. The plurality of optimal component models is applied to the spectral region associated with the optimal component model. Different optimal component empirical models may be associated with different identified spectral regions of the body of water. Further, in some instances the water quality parameters may include parameters other than Chl-a, such as clarity, turbidity, sediment concentration, or Colored Dissolved Organic Matter (CDOM).

An ensemble machine learning modeling system or ensemble machine learning algorithm is applied to the plurality of models. The ensemble machine learning system or ensemble machine learning algorithm generates an ensemble model of water quality for the body of water using the plurality of models.

In a non-limiting example, the aim of the ensemble model E is to define an appropriate ensemble function $f$ through combination or selection strategy, which could synergistically utilize the M individual empirical models to predict the Chl-a E(V) for any unknown site with the spectral band vector V: $E(V)=f\{e_1(V), e_2(V), \ldots, e_m(V)\}$. An empirical water quality model relates Chl-a concentration to the spectral index defined as band ratios or different band combinations by a linear regression function: Chl-a=a+b*(spectral index), where a is the intercept and b is the slope of the linear empirical model.

Figure 10:
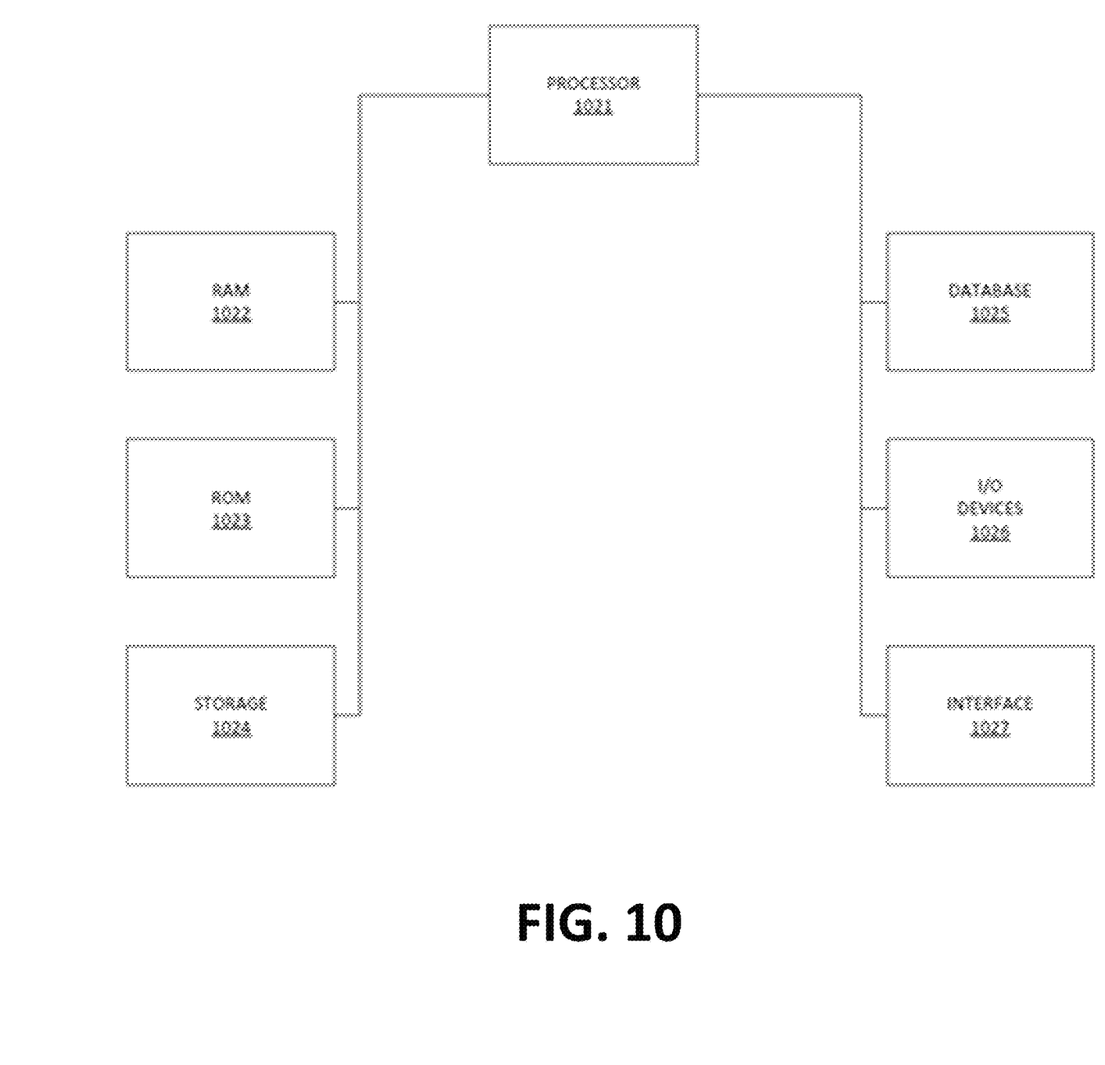
FIG. 10 illustrates an exemplary computer that may comprise all or a portion of a modeling system, an ensemble machine learning system, and/or a separate control system; conversely, any portion or portions of the computer illustrated in FIG. 10 may comprise all or a portion of a modeling system, an ensemble machine learning system, and/or a separate control system.

FIG. 10 illustrates an exemplary computer that may comprise all or a portion of an ensemble machine learning modelling system 1053, and the plurality of modeling systems 1052. Conversely, any portion or portions of the computer illustrated in FIG. 10 may comprise all or an ensemble machine learning modelling system 1053, and the plurality of modeling systems 1052. As used herein, "computer" may include a plurality of computers. The computers may include one or more hardware components such as, for example, a processor 1021, a random-access memory (RAM) module 1022, a read-only memory (ROM) module 1023, a storage 1024, a database 1025, one or more input/output (I/O) devices 1026, and an interface 1027. Alternatively, and/or additionally, the computer may include one or more software components such as, for example, a computer-readable medium, including computer executable instructions for performing a method associated with the exemplary embodiments such as, for example, an algorithm for deriving optimal component models and generating an ensemble model. It is contemplated that one or more of the hardware components listed above may be implemented using software. For example, storage 1024 may include a software partition associated with one or more other hardware components. It is understood that the components listed above are exemplary only and not intended to be limiting.

Processor 1021 may include one or more processors, each configured to execute instructions and process data to perform one or more functions associated with a computer for controlling a system and/or receiving and/or processing and/or transmitting data associated with a network of measuring devices used to generate remote sensing data. Processor 1021 may be communicatively coupled to RAM 1022, ROM 1023, storage 1024, database 1025, I/O devices 1026, and interface 1027. Processor 1021 may be configured to execute sequences of computer program instructions to perform various processes. The computer program instructions may be loaded into RAM 1022 for execution by processor 1021.

RAM 1022 and ROM 1023 may each include one or more devices for storing information associated with operation of processor 1021. For example, ROM 1023 may include a memory device configured to access and store information associated with the computer, including information for identifying, initializing, and monitoring the operation of one or more components and subsystems. RAM 1022 may include a memory device for storing data associated with one or more operations of processor 1021. For example, ROM 1023 may load instructions into RAM 1022 for execution by processor 1021.

Storage 1024 may include any type of mass storage device configured to store information that processor 1021 may need to perform processes consistent with the disclosed embodiments. For example, storage 1024 may include one or more magnetic and/or optical disk devices, such as hard drives, CD-ROMs, DVD-ROMs, or any other type of mass media device.

Database 1025 may include one or more software and/or hardware components that cooperate to store, organize, sort, filter, and/or arrange data used by the computer and/or processor 1021. For example, database 1025 may store data related to the remote sensing data correlated with signal attenuation. The database may also contain data and instructions associated with computer-executable instructions for controlling a system (e.g., a remote sensing and modeling system) and/or receiving and/or processing and/or transmitting data associated with a network of sensor nodes used to measure water quality. It is contemplated that database 1025 may store additional and/or different information than that listed above.

I/O devices 1026 may include one or more components configured to communicate information with a user associated with computer. For example, I/O devices may include a console with an integrated keyboard and mouse to allow a user to maintain a database of digital images, results of the analysis of the digital images, metrics, and the like. I/O devices 1026 may also include a display including a graphical user interface (GUI) for outputting information on a monitor. I/O devices 1026 may also include peripheral devices such as, for example, a printer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1027 may include one or more components configured to transmit and receive data via a communication network, such as the Internet, a local area network, a workstation peer-to-peer network, a direct link network, a wireless network, or any other suitable communication platform. For example, interface 1027 may include one or more modulators, demodulators, multiplexers, demultiplexers, network communication devices, wireless devices, antennas, modems, radios, receivers, transmitters, transceivers, and any other type of device configured to enable data communication via a wired or wireless communication network.

The figures illustrate the architecture, functionality, and operation of possible implementations of systems, methods and computer program products according to various implementations of the present invention. In this regard, each block of a flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated.

Any combination of one or more computer readable medium(s) may be used to implement the systems and methods described hereinabove. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

EXAMPLES

Appendix A, attached hereto, incorporated by reference, and made a part hereof includes non-limiting examples of modeling water quality using an ensemble model.

What is claimed is:

1. A method for generating an ensemble model of water quality for a body of water, comprising:
   obtaining multispectral images of the body of water;
   applying spectral space partition rules to the multispectral images of the body of water to identify one or more spectral regions of the body of water;
   associating each of the identified one or more spectral regions of the body of water, based on one or more optical characteristics of each identified spectral region of the body of water, with a selected one of a plurality of optimal component empirical models with each of the identified spectral regions of the body of water for determining water quality parameters of each identified spectral region, wherein different optimal component empirical models may be associated with different identified spectral regions of the body of water;
   applying each of the selected one of the plurality of optimal component empirical models to its associated spectral region;
   applying an ensemble machine learning algorithm to the plurality of optimal component empirical models to generate the ensemble model of water quality for the body of water; and
   globally calibrating each of the optimal component empirical models using a set of squared residuals, wherein the set of squared residuals are determined by comparing a set of empirical measurements with a set of corresponding predictions generated by the optimal component empirical models, performing a summation of the set of squared residuals, and minimizing the summation of the summation of the set of squared residuals.

2. The method of claim 1, wherein the plurality of optimal component empirical models are developed by:
   measuring a plurality of water quality parameters in a geographic region;
   applying modelling techniques to the water quality metrics to generate a plurality of models; and
   constructing the plurality of optimal component empirical models from the plurality of models.

3. The method of claim 2, wherein the plurality of water quality parameters include clarity, turbidity, sediment concentration, Chl-a, or CDOM.

4. The method of claim 2, wherein each of the optimal component empirical models are constructed by an optimization process specific to a subsection of the spectral region.

5. The method of claim 1, wherein the optimal component empirical models are generated by an iterative K-fold partition approach.

6. The method of claim 5, wherein a machine learning modeling system identifies the most accurate model by applying the spectral space partition rules built as a decision tree (the ensemble function).

7. The method of claim 1, wherein the ensemble model synergistically combines the plurality of optimal component empirical models to generate the ensemble model of water quality for the body of water.

8. The method of claim 1, wherein the ensemble model of water quality for the body of water predicts a Chl-a concentration at a site in the body of water where the Chl-a concentration is unknown.

9. The method of claim 1, wherein the plurality of optimal component empirical models are heterogeneous empirical models.

10. A system for generating an ensemble model of water quality, comprising:
    a plurality of measuring devices configured to generate plurality of multispectral images of a body of water;
    a plurality of modeling systems operably connected to the plurality of measuring devices, said modeling systems configured to generate a plurality of component empirical models;
    an ensemble machine learning modeling system operably connected to the plurality of modeling systems, the ensemble machine learning modelling system configured to:
      generate a plurality of optimal component empirical models from the plurality of component empirical models;
      apply spectral space partition rules to the multispectral images of the body of water to identify one or more spectral regions of the body of water;
      associate each of the identified one or more spectral regions of the body of water, based on one or more optical characteristics of each identified spectral region of the body of water, with a selected one of a plurality of optimal component empirical models with each of the identified spectral regions of the body of water for determining water quality parameters of each identified spectral region, wherein different component empirical models may be associated with different identified spectral regions of the body of water;
      apply each one of the selected one of the plurality of optimal component empirical models to its associated spectral region;

applying an ensemble machine learning algorithm to the plurality of optimal component empirical models to generate the ensemble model of water quality for the body of water; and globally calibrating each of the optimal component empirical models using a set of squared residuals, wherein the set of squared residuals are determined by comparing a set of empirical measurements with a set of corresponding predictions generated by the optimal component empirical models, performing a summation of the set of squared residuals, and minimizing the summation of the summation of the set of squared residuals.

11. The system of claim 10, wherein the ensemble machine learning modeling system is configured to develop the plurality of optimal component empirical models by:

measuring a plurality of water quality parameters in a geographic region;

applying modeling techniques to the water quality metrics to generate a plurality of models; and constructing the plurality of optimal component empirical models from the plurality of models.

12. The system of claim 11, wherein the plurality of water quality parameters include clarity, turbidity, sediment concentration, Chl-a, or CDOM.

13. The system of claim 11, wherein each of the optimal component empirical models are constructed by an optimization process specific to a subsection of the spectral region.

14. The system of claim 10, wherein the machine learning modeling system is configured to generate the optimal component empirical models by applying an iterative K-fold partition approach.

15. The system of claim 14, wherein the machine learning modeling system identifies the most accurate model by applying the spectral space partition rules built as a decision tree (the ensemble function).

16. The system of claim 10, wherein the ensemble model synergistically combines the plurality of optimal component empirical models to generate the ensemble model of water quality for the body of water.

17. The system of claim 10, wherein the system is configured to generate an ensemble model of water quality that predicts a Chl-a concentration at a site in the body of water where the Chl-a concentration is unknown.

18. The system of claim 10, wherein the plurality of optimal component empirical models are heterogeneous empirical models.

19. A non-transitory computer-readable medium with computer-executable instructions stored thereon, said computer-executable instructions for performing a method of generating an ensemble model of water quality for a body of water, said method comprising:

obtaining multispectral images of the body of water;

applying spectral space partition rules to the multispectral images of the body of water to identify one or more spectral regions of the body of water;

associating each of the identified one or more spectral regions of the body of water, based on one or more optical characteristics of each identified spectral region of the body of water, with a selected one of a plurality of optimal component empirical models with each of the identified spectral regions of the body of water for determining water quality parameters of each identified spectral region, wherein different optimal component empirical models may be associated with different identified spectral regions of the body of water;

applying each of the selected one of the plurality of optimal component empirical models to its associated spectral region;

applying an ensemble machine learning algorithm to the plurality of optimal component empirical models to generate the ensemble model of water quality for the body of water; and globally calibrating each of the optimal component empirical models using a set of squared residuals, wherein the set of squared residuals are determined by comparing a set of empirical measurements with a set of corresponding predictions generated by the optimal component empirical models, performing a summation of the set of squared residuals, and minimizing the summation of the summation of the set of squared residuals.

20. The computer-readable medium of claim 19, wherein the plurality of optimal component empirical models are developed by:

measuring a plurality of water quality parameters in a geographic region;

applying modelling techniques to the water quality metrics to generate a plurality of models; and constructing the plurality of optimal component empirical models from the plurality of models.

21. The computer-readable medium of claim 20, wherein the water quality parameters include clarity, turbidity, sediment concentration, Chl-a, or CDOM.

22. The computer-readable medium of claim 20, wherein each of the optimal component empirical models are constructed by an optimization process specific to a subsection of the spectral region.

23. The computer-readable medium of claim 19, wherein the optimal component empirical models are generated by an iterative K-fold partition approach.

24. The computer-readable medium of claim 23, wherein a machine learning modeling system identifies the most accurate model by applying the spectral space partition rules built as a decision tree (the ensemble function).

25. The computer-readable medium of claim 19, wherein the ensemble model synergistically combines the plurality of optimal component empirical models to generate the ensemble model of water quality for the body of water.

26. The computer-readable medium of claim 19, wherein the ensemble model of water quality for the body of water predicts a Chl-a concentration at a site in the body of water where the Chl-a concentration is unknown.

27. The computer-readable medium of claim 19, wherein the plurality of optimal component empirical models are heterogeneous empirical models.

* * * * *